United States Patent [19]

Sielaff et al.

[11] 4,288,543
[45] Sep. 8, 1981

[54] METHOD AND APPARATUS FOR IDENTIFYING MICROORGANISMS

[75] Inventors: Bruce H. Sielaff, Gales Ferry; Julius Praglin, East Lyme; James E. McKie, Jr., Ledyard; David K. Longhenry, East Lyme; Alan C. Curtiss, Old Lyme; Charles B. Bidwell, Madison, all of Conn.

[73] Assignee: Pfizer Inc., New York, N.Y.

[21] Appl. No.: 842,736

[22] Filed: Oct. 17, 1977

Related U.S. Application Data

[63] Continuation-in-part of Ser. No. 763,719, Jan. 28, 1977, abandoned.

[51] Int. Cl.³ .......................... C12Q 1/04; C12Q 1/12; C12Q 1/10; C12M 1/34
[52] U.S. Cl. ...................................... 435/34; 435/37; 435/38; 435/291
[58] Field of Search .................. 435/29, 30, 3, 32, 33, 435/291, 34, 38, 37; 422/63, 64, 65; 364/413

[56] References Cited

U.S. PATENT DOCUMENTS

| | | | |
|---|---|---|---|
| D. 230,587 | 3/1974 | Praglin et al. | D16/2 C |
| 3,804,720 | 4/1974 | Curby | 435/34 |
| 3,832,532 | 8/1974 | Praglin et al. | 364/413 |
| 3,895,661 | 7/1975 | Praglin et al. | 141/241 |
| 3,899,011 | 8/1975 | Curtiss | 141/325 |
| 3,901,588 | 8/1975 | Longhenry | 350/314 |
| 3,934,753 | 1/1976 | Curtiss | 221/3 |
| 3,942,899 | 3/1976 | Longhenry | 356/234 |
| 4,024,530 | 5/1977 | Hughes | 435/291 |
| 4,101,383 | 7/1978 | Wyatt et al. | 435/291 |

OTHER PUBLICATIONS

Buch et al., "Automated, Rapid Identification of Bacteria by Computer Analysis of Growth Inhibition Patterns with Auto Bac I," Fifteenth Interscience Conference on Artimicrobial Agents and Chemotherapy, Sponsered by Am. Soc. for Micro, Sep. 24-26, 1975.
Sielauff et al., "Computer-Assisted Bacterial Identification Utilizing Anti Microbial Susceptibility Profiles Generated by Auto Bac I," *J. Clin. Micro.*, vol. 3, No. 2, (Feb. 1976), pp. 105–109.
Friedman et al., "Computer Identification of Bacteria on the Basis of their Antibiotic Susceptibility Patterns", *Applied Microbiol.*, vol. 26, No. 3, (1973), pp. 314–317.
Sutter et al., "Antibiotic Disc Susceptibility Test for Rapid Presumptive Identification of Gram-Negative Anaerobic Bacilli", *App. Microbiol.*, vol. 21, No. 1, (1971), pp. 13–20.
Elek, S.D. et al., "Resistogram Typing-A New Epidemiological Tool: Application to Escherichia Coli",*J. Med. Microbial.*, 3, 1979, (pp. 103–110).
Kashbur, I. M. et al., "Resistotyping of Proteus Mirabilis and a Comparison with Other Methods of Typing", *J. Clin, Path.*, 27, 1974, (pp. 572–577).
Sielaff, B. et al., "Rapid Automatic Bacterial Identification System with Autobac I", Abstract of paper presented at International Conf. on Mechanized Microbiology, Ottawa, Canada, Sep. 10, 1975.
McGowan, J. Jr., et al. "Rapid Semiquantitative Testing of Antibiotic Susceptibility: Use of a Multicell Disk Elution System Antimicrob Agents & Chemother", 7(5) pp. 543–547, (May 77).

*Primary Examiner*—Thomas G. Wiseman
*Attorney, Agent, or Firm*—Connolly and Hutz

[57] ABSTRACT

The method and apparatus for testing the susceptibility of bacteria to antibiotics described in the U.S. Pat. No. 3,832,532 and related patents are adapted for identifying various strains of bacteria by determining the light scatter indices (LSI) for a special group of antimicrobials, which have particularly significant characteristics with respect to identifying the strains of microorganisms, and analyzing them by a computer method, such as a quadratic discriminant function statistical technique, to identify the microorganisms to which the antimicrobials are applied. It has been found that 14 antimicrobial agents provide an extremely reliable identification and it is believed that the identifying group of agents could be reduced without sacrificing too much reliability. The agents preferably should be those which are not in common therapeutic use to avoid errors resulting from strains which have become immune to various therapeutically-utilized antibiotic agents. A presently defined group of such agents includes approximately 36 members (later described herein of which a number can be selected for reliable identification purposes by statistical techniques).

4 Claims, 2 Drawing Figures

METHOD AND APPARATUS FOR IDENTIFYING MICROORGANISMS

CROSS REFERENCE TO RELATED APPLICATIONS

This application is a continuation-in-part of commonly assigned copending application Ser. No. 763,719 filed Jan. 28, 1977, now abandoned.

BACKGROUND OF THE INVENTION

The concept of using growth inhibitory or antibacterial susceptibility patterns for bacterial identification is not entirely new. In 1971 Gilardi (Gilardi, G. L., 1971; Appl. Microbiol. 22:821-823) found that susceptibility profiles could be used to assist in the identification of lactose-nonfermenting, gram-negative bacteria. He used susceptibility information, for 16 antibiotics, obtained from the disk agar diffusion method. Sutter and Finegold (Sutter, V. L., and S. M. Finegold, 1971; Appl. Microbiol. 21:13-20) used susceptibility profiles to place gram-negative anaerobic bacilli into five different groups. Further testing was then required to complete the identification.

A Baysean mathematical model was used by Friedman and MacLowry (Friedman, R., and J. MacLowry, 1973; Appln. Microbiol. 26:314-317) to classify bacteria. Their data base contained probability data on the susceptibility profiles of 31 species of bacteria. This data was collected over a period of several years. When 1,000 clinical isolates were classified by this method, there was an 86% agreement with the identification obtained by conventional biochemical procedures.

U.S. Pat. No. 3,832,532 describes a method and apparatus for testing antibiotic susceptibility in conjunction with a determination of the light scatter index (LSI) of the bacteria being tested. Auxiliary methods and equipment for use in such determinations are described in the following U.S. Pat. Nos.: 3,832,532; 3,895,661; 3,899,011; 3,901,588; 3,934,753; 3,942,899; and U.S. Pat. No. De. 230,587. The equipment described in the aforementioned system combines the speed of automation with the flexibility of manual procedures. It is designed to determine the susceptbility of a bacteria to a panel of up to 12 antimicrobial agents simultaneously. The result for each antimicrobial is an index of susceptibility called the "light scatter index" (LSI). The index runs from 0.00 (resistant) to 1.00 (susceptible) in increments of 0.01. The test results, except for certain slow-growing organisms, are available within 3 to 5 hours after the test is begun. An object of this invention is to provide a method and apparatus and suitable identifying agents for use in identifying bacteria in accordance with a determination of LSI values of sample solutions reacted with the agents.

SUMMARY

In accordance with this invention a selected number, such as 10 to 14, of a group of about 36 special organism growth-inhibiting agents, such as antimicrobial agents (later described) is utilized in determining growth LSI values for sample solutions of bacteria reacted with the agents. The numerical growth data obtained by the light scatter comparisons are analyzed, such as by computer-assisted techniques, to identify the strains of bacteria. A highly useful method for computer use is the quadratic discriminant function statistical technique. This technique is part of the preferred embodiment of this invention but other statistical methods can be employed with lesser degrees of success.

This methodology is particularly well adapted for use with the method and apparatus of U.S. Pat. No. 3,832,532, but may also be adapted by anyone knowledgeable in the field to be used with any method of susceptibility testing that provides reasonably quantitative measurement of organism growth in the presence of inhibitory substances.

The methodology described in U.S. Pat. No. 3,837,746 may probably also be adapted to be used with this method if identifying bacteria.

The invention, therefore, is not restricted to the apparatus described in the patents referred to above but may be used with any method of testing capable of quantitating bacterial growth with respect to various inhibitory agents. A preferred embodiment is the combination of the analysis method described below with a rapid susceptibility system, such as described in U.S. Pat. No. 3,832,532. However the general usefulness of the concept is not restricted to any particular quantitative susceptibility methodology, rapid or conventional.

"LSI" refers to the quantitative inhibitory index generated by the Autobac susceptibility testing system. However this index may be replaced by any other suitably scaled quantitative growth index generated by another test system with no loss in applicability.

BRIEF DESCRIPTION OF THE DRAWING

Novel features and advantages of the present invention will become apparent to one skilled in the art from a reading of the following description in conjunction with the accompanying drawing wherein similar reference characters refer to similar parts and in which.

DESCRIPTION OF THE PREFERRED EMBODIMENT

Figure 1:
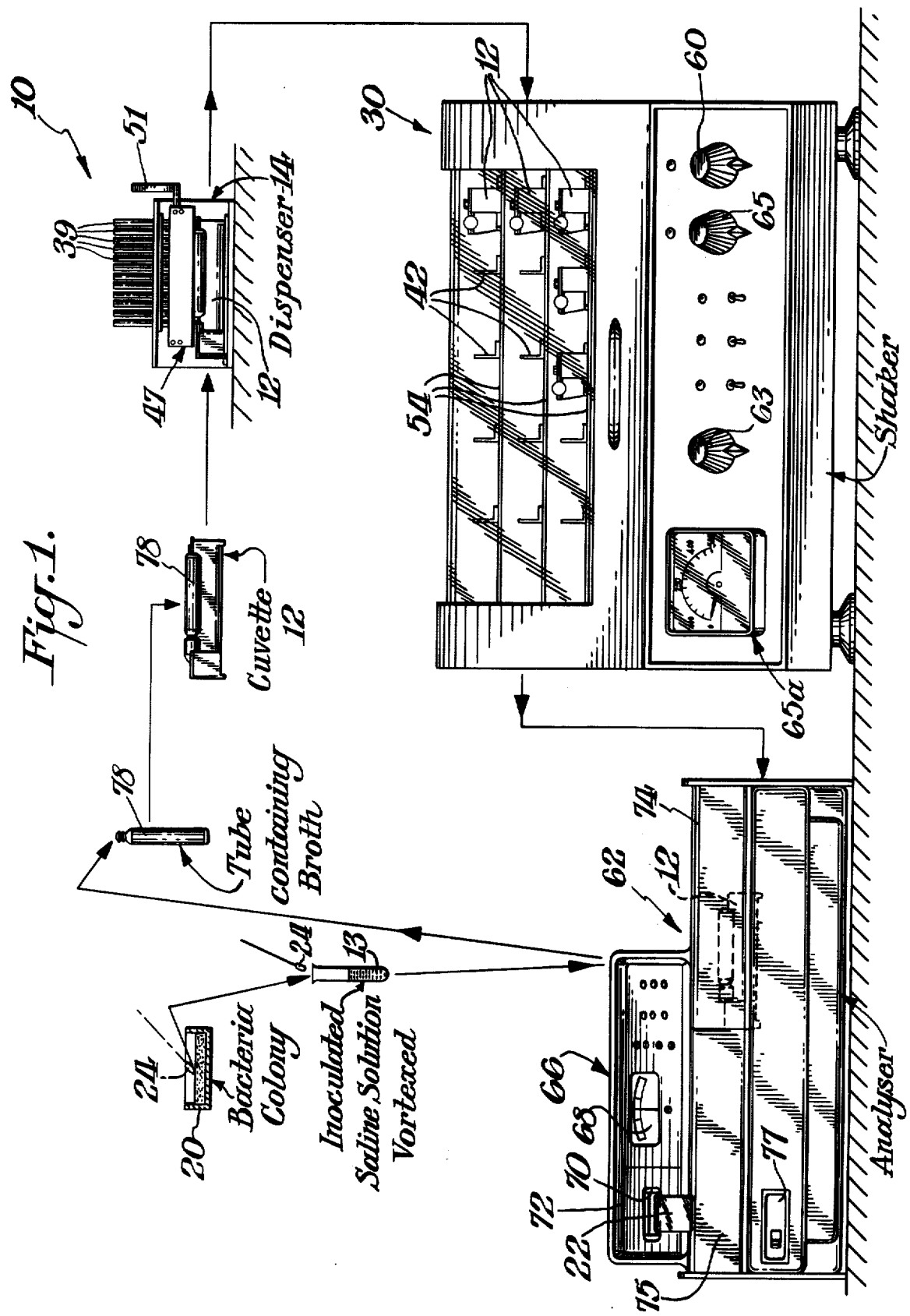
FIG. 1 is a partially schematic diagram of apparatus associated to perform the method of this invention and some of which comprise embodiments of apparatus aspects of this invention.

As shown in FIG. 1, prior system 10 for determining the relative effectiveness of a number of different antibiotics (12 for example) to inhibit the growth of bacteria includes: a disposable plastic cuvette 12 in which the susceptibility tests are performed, a disc dispenser 14 for inserting discs into cuvette 12, an incubator-shaker 30 for incubating and agitating the cuvettes and an automatic light-scattering photometer analyzer 62 for evaluating bacterial growth and printing the results on a preprinted form or tape 22 as described in detail in U.S. Pat. No. 3,832,532. However, other methods of evaluating growth may be employed such as optical absorbance, cell counting, impedance measurement, ATP concentration, radio isotope uptake or generation from labeled compounds, oxygen uptake, $CO_2$ production, heat production, and chemical reactions due to metabolic utilization or waste metabolites. While these methodologies may differ in convenience and accuracy, this invention teaches that the identification methodology is independent of the methodology used to enumerate growth or assess the degree of inhibition as long as the method is capable of obtaining a quantative enough result to be used in the statistical evaluation.

Prior to the test procedure described herein in detail, a clinical isolate is obtained, transferred to a Petri dish 20 and incubated overnight. Several colonies of similar morphology are then picked from the plate by the bacteriologist using loop 24 and suspended via vortexing in saline solution in tube 13. This step can be omitted in certain cases when a single organism is likely to have caused the infection. In such a case the inoculum can be prepared in suitable dilution from centrifuged blood, cerebrospinal fluid, or filtered urine. By use of the photometer instrument's standardizing mode, the suspension in tube is made up to a standard bacterial concentration which is checked in analyzer 62 by insertion in a port in cover 74 and read on meter 68. Two ml. of the above suspension is added to 18 ml. of eugonic broth in a screw top test tube 78. Test tube 78 screws on to plastic cuvette 12, and a simple manipulation transfers the test tube contents evenly to thirteen cuvette test chambers. Antimicrobials preferably absorbed on paper discs are now added by disc dispenser 14 through ports, uncovered by removal of the closure, and are held suspended in the growth medium in twelve disconnected lobes of the chambers by plastic tubular fingers in the cuvette top. The thirteenth chamber is the control. Cuvette 12 is now incubated preferably for 3 hours in an incubator-shaker 30 designed to hold up to 30 cuvettes. At the end of 3 hours, a cuvette 12 is inserted in analyzer instrument 62, and the growth in each chamber is evaluated. By comparison to the control chamber, the relative inhibitory effect of each antimicrobial is calculated and printed as described in detail in U.S. Pat. No. 3,832,532.

The following parts are described in detail in U.S. Pat. No. 3,832,532: cartridge tubes 39; holding brackets 42; lever 51; racks 54; safety thermostat 60; speed control knob 63; temperature control knob 65; meter 65a; control panel 66; printer slot 70; instrument housing 72; door 75; power switch 77.

Figure 2:
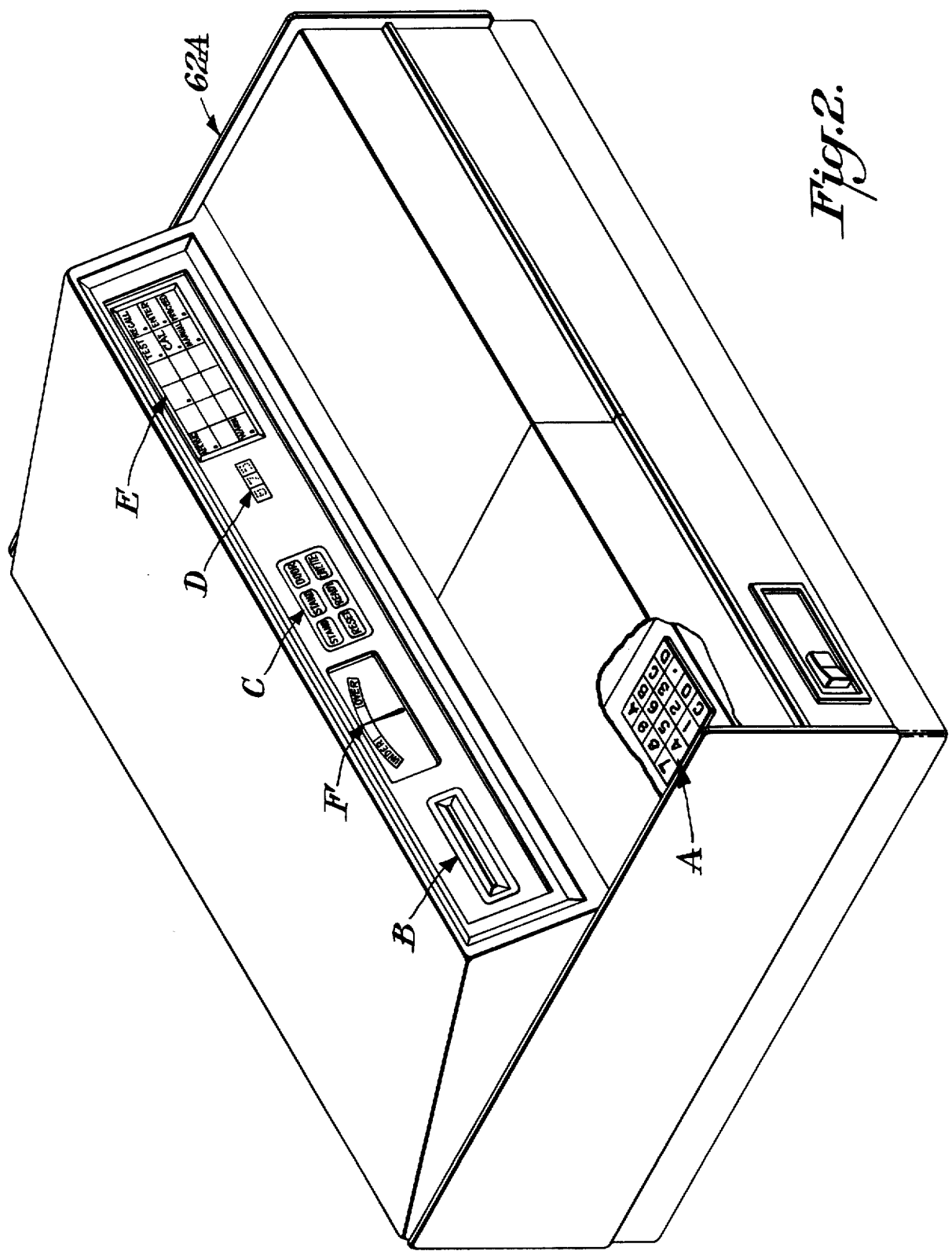
FIG. 2 is a three-dimensional view of one form of apparatus which constitutes the central console of one embodiment of this invention.

In FIG. 2 is shown console 62A for practicing this invention which is similar to apparatus described in U.S. Pat. No. 3,832,532 in conjunction with the apparatus and methods described in the other related patents referred to herein. Console 62A has the following similarities and differences from the apparatus described in the '532 patent.

1. Front Panel: The size of the front panel was extended the full width of the instrument to allow room for Keyboard E and Numerical Display D.

2. The former set of switches used to set the machine background constant was replaced by Key-pad A.

3. Printer slot, B; Inoculum Meter, F; and Control Panel C are essentially unchanged.

The mode of operation is as follows:

1. Once a procedure has been selected and the background constant entered, the operation of the machine is exactly the same as described in the '532 patent.

2. The mode of operation is selected by pressing the appropriate buttons on Keyboard E. For example, the machine is set up to perform a standard susceptibility test by pressing in sequence the buttons marked AEROBIC SUSCEPT TEST. As the button is pressed, the appropriate indicator light is lit to indicate the selected instrument mode. An aerobic identification test mode would be initiated, for example, by pressing in sequence AEROBIC IDENT TEST.

3. Calculation and entering of the background constant is initiated by indicating the test mode desired by pressing CAL instead of TEST. Thus, to calculate the background constant required in the present susceptibility procedure, press AEROBIC SUSCEPT CAL. The operator then runs two or more cuvettes inoculated in the manner prescribed for calibration. The machine automatically computes the chamber average for each cuvette and the grand average for all cuvettes run and displays this number on Digital Display D. If this number is satisfactory to the operator, he presses ENTER on Keyboard E and the number is retained in memory for use in the procedure. Pressing TEST returns the machine to the normal operating mode.

If a background constant of specific value is required, this may be entered via Key-pad A and the ENTER button on Keyboard E.

Any cuvette which has more than two chambers differing from the average light-scatter value computed, by more than a predetermined amount, is automatically rejected and the operator is requested to run an additional cuvette.

4. The blank spaces provided in Keyboard E allow up to 20 additional procedures to be added to the machine by activating the blank buttons and adding modular plug-in circuitry internally.

The method of this invention is practiced in the following manner. The plastic cuvettes, described in U.S. Pat. No. 3,895,661 and U.S. Pat. No. De. 230,587, which are stored in plastic bags, are removed from their containers. A white, flexible plastic closure is stripped back from the top of the cuvette. The cuvette is then inserted into the disc dispenser, such as described in U.S. Pat. No. 3,899,011, and the disc dispenser is activated, releasing selected antimicrobic discs into each of the chambers of the cuvette. Only one disc is delivered to each chamber, and the material contained within that disc has been previously selected from either antimicrobial susceptibility or for the capacity to differentiate between bacterial species. The white strip closure is then replaced on the cuvette.

The next step is to select a bacterial strain from the primary isolation plate. A colony is inoculated into a tube of preferably phosphate buffered saline. This saline tube is then inserted into the light scattering photometer, again part of the basic central component of the system, in order to standardize the inocula and the standardization meter needle is observed for deflection. When the needle registers in the center portion of the marked gage, the standardization has occurred. Two ml. of the standardized inoculum are then pipetted into a tube of Eugonic broth. While holding the cuvette vertically, the Eugonic broth tube is screwed into the cuvette. The cuvette is then inverted on a level surface so that all of the broth contained in the Eugonic broth tube is distributed to a holding chamber which is on one end of the cuvette. As this procedure occurs, the cuvette stands vertically on end. Two further manipulations of the cuvette are made, (1) to distribute the broth evenly along the length of the cuvette, and (2) to deliver equal 1½ ml. aliquots of the broth into the individual chambers of the cuvette, which have previously been armed with the antimicrobic discs.

The cuvette is then placed in the incubator shaker, and is rotated at 220 rotations/minute in a 36° environment for approximately three hours. At the conclusion of the incubation period, the cuvette is placed on a holding bar or carriage in the light scattering photometer component of the system. The photometer lid is closed, a card is inserted for purposes of recording the results, and the machine then begins its computation.

Sufficient growth must be obtained in the control chamber or the photometer will automatically reject the test. In the event of such a rejection, the cuvette is returned to the incubator and incubated for an additional period of time. If there is sufficient growth in the control chamber, then a light scatter index is calculated by means of a mini-computer within the photometer housing. This light scatter index is a numerical value between 0 and 1, and based on this numerical value, an interpretation of susceptible, intermediate, or resistant is calculated for each antimicrobial agent.

As mentioned previously, the results of susceptibility testing with this system have been shown to compare favorably with both the standardized Kirby-Bauer disc diffusion method (Bauer, A. W., W. M. M. Kirby, J. C. Sherris, and M. Turck, 1966; Am. J. Clin. Path. 45:493–496; and National Committee For Clinical Laboratory Standards Subcommittee on Antimicrobial Susceptibility Testing, 1974; In A. Balows (ed.)., *Current Techniques for Antibiotic Susceptibility Testing.* Charles C. Thomas, Springfield, Ill., p. 138-155) and with the International Collaborative Study standardized agar dilution technique (Ericsson, H., and J. C. Sherris, 1971; Acta. Pathol. Microbiol. Scand. Suppl. 217).

This procedure is not, however, restricted to the use of the above system but will perform equally well with other growth measuring systems provided that such systems can perform adequate quantative antimicrobial measurement.

The identification method utilizes the results from each antimicrobic tested. The light scatter index, which extends from $-0.5$ to $1.5$ in increments of $0.01$ is utilized in a multivariate analysis procedure called the Quadratic Discriminant Function (QDF). This is the preferred embodiment but not the only possible embodiment of the invention. The QDF is based on the assumption that members of each of the bacterial groups tend to follow a characteristic normal distribution with each of the antimicrobial compounds tested and used in the analysis system (Sielaff, B. H., Johnson, E. A. and Matsen, J. M, 1976; J. Clin. Microbiol (3:105–109)). If two groups of bacteria happen to have overlapping distribution curves, then a point of equal probability is created in the overlap region. This point of equal probability can be used as a boundary for classification. If there is considerable overlap, then even a sophisticated computer technique cannot separate the groups of bacteria with one variable. As one adds variables, then a greater likelihood of separation of groups occurs. If the groups to be separated have widely differing values with each of the several antimicrobial agents, then misclassification is minimized, and identification is rather straightforward and easily accomplished.

The objective, therefore, is to find compounds which have an ability to discriminate widely on the basis of light scatter index values achieved with each of the antimicrobial agents used, or to have at least one antimicrobic upon which a clearcut discrimination occurs. Initial efforts were concerned with the use of only those agents which have been used therapeutically in humans against bacterial organisms. Work was commenced with the gram-negative organisms because of the projected greater difficulty in separating these organisms into the various clinically significant species. This group of organisms contains genera that are difficult to separate, such as Citrobacter, Enterobacter, Escherichia and Klebsiella, as well as the four species of the Proteus genus. The antimicrobial compounds employed in the profile were ampicillin, bacitracin, two concentrations of carbenicillin, cephalothin, colistin sulfate at two concentrations, erythromycin, furazolidone, kanamycin, methenamine mandelate, malidixic acid, neomycin, nitrofurantoin, novobiocin, polymixin B, streptomycin, and tetracycline. The matrices or date base, utilized in the quadratic discriminant function computer program to analyze the results of testing, were generated by inputing to the computer the light scatter index values from known organisms within these bacterial groupings.

Utilizing this 18-agent profile, with the 481 organisms tests, an accuracy of this profile of 97.3% was achieved.

Problems, however, exist with respect to the size of this profile, with respect to the limited number of species involved in the identification procedure, and with respect to the fact that one always has the worry that spontaneous resistance might occur in a hospital environment to agents being used therapeutically on the bacterial organisms found within the human patient population, or within the environment as a whole, as for example, in animal feeds, in veterinary medicine, etc.

The next step in the study, then, was to attempt to decrease the antimicrobic profile, in order to decrease the number of variables to a minimum without sacrificing percentage agreement. In this particular endeavor, there were various subsets of different sizes of the 18 original antimicrobics which were utilized. One particular grouping of 14 antimicrobial agents, used the 481 organisms previously discussed. There was a loss in percent agreement of less than 2%. As the number of variables was decreased below 14, however, the percentage agreement began to drop rapidly. For all intents and purposes, then, utilizing this particular approach, the subset of 14 antimicrobials appeared to represent the smallest group which still gave an acceptable level of agreement. Again, in this subset are only agents which are utilized therapeutically.

The next attempt was to develop a repetoire of agents which have antimicrobial action, but which do not fit into the classic category of antibiotic or therapeutic antimicrobial compounds. In this portion of the investigation, there were reviewed well over 600 compounds for potential antibacterial activity. Included in the list of compounds considered were chemicals of all types, which has been reported to have any kind of antibacterial spectrum. Of the compounds reviewed, approximately 15% were selected for screening to determine their differential selectivity as to antibacterial spectrum, with 104 compounds actually being screened against 20 different species, including the majority of the Enterobacteriaceae, as well as commonly isolated members of the non-fermenter gram-negative groups. These compounds were tested by means of minimal inhibitory concentration studies in order to determine the levels at which antibacterial activity occurred in the several members of each group included in the screening. Over 10,000 sets of minimal inhibitory concentration studies were performed. Those compounds which showed capacity for differentiating bacterial groups, were then considered for further analysis within the actual computer system.

The initial step in this direction was to use a small number of these compounds, along with a profile of the previously investigated agents, to test for discriminatory ability. Twelve compounds were utilized in this particular segment of the investigation, and these compounds included four compounds substituted for classic antibiotic agents. The four substituted compounds include brilliant green, chlorhexidine, cycloserine and trihydroxyacetophehone. Also included is methenamine madelate, an agent not incuded in routine antimicrobial susceptibility profiles, but which has been shown in our system to be very helpful in the differentiation profiles. Fourteen of the original twenty bacterial groups, with 24 or 25 isolates per group, were then utilized to test the capacity to separate these commonly isolated, and somewhat difficult to separate, groups. Purposely included again were organisms which pose problems in separation such as the Escherichia, Citrobacter, Enterobacter, and Proteus genera.

Utilizing the above set of antimicrobials against these organisms, an accuracy of 97.1% was achieved by the computer program, using the calculated rules. The poorest results were with the *Escherichia coli*, where only 20 of the 24 strains were correctly identified. Three *Citrobacter freundii* organisms were misidentified as was one Enterobacter strain and two *Proteus vulgaris* strains. The problem as it occurs with *Escherichia coli* is one of separating it from the Shigella genus. Of the compounds which were screened by us, agents do exist which will separate these particular genera. If this factor is taken into consideration then, the accuracy within the identification schemes for these 14 species would approach more nearly 98 to 99%.

The basic feature of these studies was to determine the feasibility of using machine-readable bacterial growth, as it may or may not occur in the presence of various chemical compounds, for creating an identification profile of bacteria. This objective has been successfully accomplished. Considerable time over the past two years has been spent in identifying compounds which may be useful and in creating a computer program which will successfully employ the machine-generated values. To prevent a dilution of effort in a feasibility study, it was necessary to limit the number of groups studied. We have focused on the gram-negative bacteria in our formal studies for several reasons. First, the gram strain is a fairly quick and easy-to-perform method of differentiating this group from other bacterial groups. Secondly, the members of this group are generally the most difficult to identify in the clinical microbiology laboratory. They provide the greatest challenge for the proposed identification system. Thirdly, gram-negative bacteria comprise the majority of identification being done currently in the clinical microbiology laboratory.

In summary, studies have shown that an automated instrumental method for antimicrobial susceptibility testing, can be utilized to provide bacterial identification in the same 3-5 hour time frame employed for susceptibility testing. The identification system utilized antimicrobial susceptibility results and growth patterns from other growth-no growth chemical substances. A computer program has been developed which analyzes these results by means of the Quadratic Discriminant Function statistical technique. Accuracy of identification for various taxonomic groupings of bacteria is 95% or greater, as compared to standard biochemical methods.

The following is a list of effective antimicrobial agents and effective concentrations which can be effectively utilized in the method of this invention.

| Compound | Disc Mass | Range of Effective Concentrations in Micrograms per ml. |
|---|---|---|
| Acriflavine | 7.5 mcg | 5.0 |
| Acriflavine | 30.0 mcg | 20.0 |
| 9-Aminoacridine | 10.0 mcg | 6.7 |
| Auramine O | 160.0 mcg | 106.7 |
| Brilliant Green | 1.5 mcg | 1.0 |
| Brilliant Green | 3.0 mcg | 2.0 |
| Brilliant Green | 5.0 mcg | 3.3 |
| Cetrimide | 120.0 mcg | 80.0 |
| Cobalt Chloride | 375.0 mcg | 250.0 |
| Cupric Chloride | 375.0 mcg | 250.0 |
| Cycloserine | 120.0 mcg | 80.0 |
| Cycloserine | 240.0 mcg | 160.0 |
| 3,5 Dibromosalicylic Acid | 750.0 mcg | 500.0 |
| Dodecylamine HCl | 18.75 mcg | 12.5 |
| Dodecylamine HCl | 75.0 mcg | 50.0 |
| 5-Fluorouracil | 8.0 mcg | 5.3 |
| Floxuridine | 9.0 mcg | 6.0 |
| Floxuridine | 36.0 mcg | 24.0 |
| Malachite Green | 3.0 mcg | 2.0 |
| Methylene Blue | 255.0 mcg | 170.0 |
| Omadine Disulfide | 5.5 mcg | 3.7 |
| Sodium Omadine | 7.5 mcg | 5.0 |
| Sodium Azide | 75.0 mcg | 50.0 |
| Thallous Acetate | 150.0 mcg | 100.0 |
| 2',3',4'-Trihydroxyacetophenone | 375.0 mcg | 250.0 |
| Bacitracin | 18.0 unit | 12.0 unit/ml |
| Carbenicillin | 50.0 mcg | 33.3 |
| Cephalothin | 15.0 mcg | 10.0 |
| Colistin | 13.0 mcg | 8.7 |
| Kanamycin | 5.0 mcg | 3.3 |
| Methenamine Mandelate | 1.0 mg | 667.0 |
| Nalidixic Acid | 5.0 mcg | 3.3 |
| Nitrofurantoin | 15.0 mcg | 10.0 |
| Novobiocin | 30.0 mcg | 20.0 |
| Polymyxin B | 50.0 unit | 33.3 unit/ml |
| Tetracycline | 0.5 mcg | 0.3 |

STATISTICAL TECHNIQUE USED FOR IDENTIFICATION

Identification is accomplished preferably by means of a multivariate statistical technique known as the quadratic discriminant function. The quadratic discriminant function is based on the multivariate normal model. Two adjacent, intersecting multivariate normal distributions have a point of equal probability in the overlap region. This point of equal probabality can be used as a boundary for classification. To clasify an individual, all that is necessary is to determine on which side of the boundary the individual falls. This equi-probability boundary minimizes mis-classification, assuming that the size of the populations are both approximately equal. If the two populations are of greatly different size, then the proportion of each population that is mis-classified will be minimized. but the total number of mis-classifications will not be minimized. An adjustment for the difference in population size would have to be made.

The procedure begins by computing the covariance matrices for the different groups. The formula for calculating the elements of the covariance matrix is the standard covariance formula as follows;

$$S_{x_i x_j} = \frac{n \sum_{k=1}^{n} x_\mu x_\mu - \sum_{k=1}^{n} x_\mu \sum_{k=1}^{n} x_\mu}{n^2 - n} \quad (1)$$

where $S_{x_{ij}}$ is the covariance between variables $x_i$ and $x_j$ (when $i=j$, the formula reduces to that of the variance of variable $x_i$) and n is the number of observations on variables $x_i$ and $x_j$ (this number is the same for both $x_i$ and $x_j$; it represents the number of individuals in the data set). These matrices contain the variances and covariances for the different variables in each group.

Also calculated are mean vectors for each group. They contain the means for the different variables in each group. If the set of variables used for classification is changed, then a new set of matrices must be constructed. These matrices will be constructed using only the LSI values for those variables in the new variable set.

For classifying an individual into one of NG groups, the following function is calculated for each group:

$$f(X)_i = p_i(2\pi)^{-\frac{NV}{2}} |S_i|^{\frac{1}{2}} e^{-\frac{qi}{2}} \quad (2)$$

where $p_i$ can be either the proportion of the sample in group i or the prior probability of group i; NV is the number of variables; $|S_i|$ is the determinant of the covariance matrix for group i; $q_i=(X-x_i)'S_i^{-1}(X-x_i)$, where X is the vector of LSI values for the organism to be classified; $x_i$ is the means vector for the $i^{th}$ group;' means the matrix transpose; and $S_i^{-1}$ is the inverse of the covariance matrix for the $i^{th}$ group. It can be seen that equation 2 without the $p_i$ is just the probability density function for the multivariate normal model.

When this has been computed for all groups, the group with the greatest value for f(X) is selected as the group identification for the unknown organism. In actual practice, since the relative magnitude, used for comparison between groups, is important rather than the actual value, the constant factor involving $\pi$ is eliminated from the calculations.

In the real world environment, most multivatiate distributions are not normal. Fortunately, the quadratic discriminant function procedure is very robust. Very good classification rules can be generated for populations that are very nonnormal. For further discussion of multivariate normality and the quadratic discriminant functions, see Anderson (Anderson, T. W., 1958; John Wiley & Sons, Inc., New York), Grams et al (Grams, R. R., E. A. Johnson, and E. S. Benson, 1972, Am. J. Clin. Pathol. 58:188–200; and Grams, R. R., E. A. Johnson, and E. S. Benson, 1972, Am. J. Clin. Pathol. 58:201–207) and Michaelis (Michaelis, J., 1973, Academic Press, Inc., New York).

RESULTS

A total of 31 antimicrobial agents were investigated. Because multiple concentrations of certain agents were used, a total of 48 possible variables (Table I) were examined in the course of these studies. Many of these variables were eliminated because they gave no information useful for differentiation. Most of the strains of all groups were either all susceptible or all resistant to the antimicrobial at that concentration. Other variables provided redundant information (the same information as another variable) and could, therefore, be eliminated. Table 2 shows the subset of the total variable set that showed the most promise.

The antimicrobials were tested against a sample of 481 bacterial isolates. The composition of this sample is shown in Table 3. These results were used to construct the matrices used for classification. When the 481 isolates in Table 3 were classified according to the 18 antimicrobials in Table 2, there was greater than 97% agreement with the identification arrived at by the clinical laboratory by conventional identification procedures. These results can be seen in Table 4. Nearly 80% of the disagreements consisted of organisms indentified as Citrobacter or Enterobacter by the clinical lab and something else by the susceptibility profile. These two genera were consistently found to be the most difficult to identify.

TABLE 1

| | | Antibiotics investigated | | | |
|---|---|---|---|---|---|
| Agent | Disk mass ($\mu$g) | Agent | Disk mass ($\mu$g) | Agent | Disk mass ($\mu$g) |
| Ampicillin | 3.6 | Kanamycin | 5.0 | Penicillin G | 0.2[a] |
| Bacitracin | 18.0[a] | Kanamycin | 18.0 | Penicillin G | 2.0[a] |
| Carbenicillin | 50.0 | Lincomycin | 2.0 | Penicillin G | 10.0[a] |
| Carbenicillin | 120.0 | Methenamine mandelate | 1.0[b] | Polymyxin B | 12.5[a] |
| Cephalothin | 15.0 | Methacycline | 30.0 | Polymyxin B | 50.0[a] |
| Chloramphenicol | 5.0 | Methicillin | 5.0 | Polymyxin B | 300.0[a] |
| Clindamycin | 2.0 | Nafcillin | 1.0 | Streptomycin | 2.0 |
| Cloxacillin | 1.0 | Nalidixic acid | 5.0 | Streptomycin | 10.0 |
| Colistin | 2.0 | Nalidixic acid | 15.0 | Streptomycin | 20.0 |
| Colistin | 13.0 | Neomycin | 5.0 | Tetracycline | 0.5 |
| Doxycycline | 0.5 | Neomycin | 20.0 | Tetracycline | 1.5 |
| Doxycycline | 1.6 | Nitrofurantoin | 15.0 | Trimethoprim/sulfamethoxazole | 1.25 23.75 |
| Erythromycin | 2.5 | Novobiocin | 5.0 | Vancomycin | 10.0 |
| Erythromycin | 15.0 | Novobiocin | 30.0 | Vancomycin | 30.0 |
| Furizolidone | 100.0 | Oleandomycin | 6.0 | Viomycin | 2.0 |
| Gentamicin | 9.0 | Oleandomycin | 15.0 | Viomycin | 10.0 |

[a] Mass measured in units.
[b] Mass measured in milligrams.

TABLE 2

| | Antibiotic subset | | |
|---|---|---|---|
| Agent | Disk mass ($\mu$g) | Agent | Disk mass 8$\mu$g) |
| Ampicillin | 3.6 | Kanamycin | 5.0 |
| Bacitracin | 18.0[a] | Methenamine mandelate | 1.0[b] |
| Carbenicillin | 50.0 | Nalidixic acid | 5.0 |
| Carbenicillin | 120.0 | Neomycin | 5.0 |
| Cephalothin | 15.0 | Nitrofurantoin | 15.0 |
| Colistin | 2.0 | Novobiocin | 30.0 |
| Colistin | 13.0 | Polymyxin B | 50.0[a] |
| Erythromycin | 15.0 | Streptomycin | 10.0 |

TABLE 2-continued

| | Antibiotic subset | | |
|---|---|---|---|
| Agent | Disk mass ($\mu$g) | Agent | Disk mass ($\mu$g) |
| Furizolidone | 100.0 | Tetracycline | 0.5 |

[a] Mass measured in units.
[b] Mass measured in milligrams.

TABLE 3

| Composition of sample | |
|---|---|
| Organism | No. of organisms |
| CITROB[a] | 50 |
| ENTEROB | 48 |
| ECOLI | 75 |
| HEREL | 35 |
| KLEB | 59 |
| PROTMIR | 49 |
| PROTOTH | 51 |
| P. morganii | (19)[b] |
| P. rettgeri | (17) |
| P. vulgaris | (15) |
| PSEUDO | 62 |
| P. aeruginosa | (35) |
| P. fluorescens | (15) |
| P. maltophilia | (12) |
| SERRAT | 52 |

[a] CITROB, Citrobacter; ENTEROB, Enterobacter; ECOLI, Escherichia coli; HEREL, Herellea; KLEB, Klebsiella; PROTMIR, Proteus mirabilis; PROTOTH, indole-positive Proteus; PSEUDO, Pseudomonas; SERRAT, Serratia.
[b] Numbers in parentheses not included in totals of organisms tested.

feasibility study, it was necessary to limit the number of groups studied. Gramnegative bacteria were focused on for several reasons. First, since the Gram strain is fairly quick and easy to perform, differentiation of this group can be accomplished with relative ease. Second, since the members of this group are generally the most difficult to identify, they would provide the greatest test for the proposed identification system. Lastly, gram-negative bacteria comprise the vast majority of organisms currently identified in the clinical microbiology laboratory.

As with most feasibility studies, questions arose during the course of the study. The principal question regarded the alteration of the susceptibility profile due to acquired resistance. This problem was not encountered during the course of the study, but nonetheless, the spector of mis-identifications due to this cause remains. Acquired resistance occurs because resistant mutants are selected for by the widespread use of an antimicrobial agent. This resistance can then be transferred through r factors.

The scope of the present identification system, can be expanded by the addition of more bacterial groups. For example, additional gram-negative genera, as well as gram-positive genera could be added. It would also be valuable if more speciation within the genera could also be accomplished. These are areas that need further investigation. Work is currently progressing in our laboratories to address the above-mentioned points. A

TABLE 4

| Group affiliation by susceptibility profile and conventional procedures - 18 variables[a] | | | | | | | | | |
|---|---|---|---|---|---|---|---|---|---|
| Group affiliation by conventional procedures | Group affiliation by susceptibility profile | | | | | | | | |
| | CITROB | ENTEROB | ECOLI | HEREL | KLEB | PROTMIR | PROTOTH | PSEUDO | SERRAT |
| CITROB | 45 | 2 | 2 | 0 | 1 | 0 | 0 | 0 | 0 |
| ENTEROB | 4 | 43 | 1 | 0 | 0 | 0 | 0 | 0 | 0 |
| ECOLI | 0 | 1 | 73 | 0 | 0 | 0 | 0 | 0 | 1 |
| HEREL | 0 | 0 | 0 | 35 | 0 | 0 | 0 | 0 | 0 |
| KLEB | 0 | 0 | 0 | 0 | 59 | 0 | 0 | 0 | 0 |
| PROTMIR | 0 | 0 | 0 | 0 | 0 | 51 | 0 | 0 | 0 |
| PROTOTH | 0 | 0 | 0 | 0 | 0 | 1 | 48 | 0 | 0 |
| PSEUDO | 0 | 0 | 0 | 0 | 0 | 0 | 0 | 62 | 0 |
| SERRAT | 0 | 0 | 0 | 0 | 0 | 0 | 0 | 0 | 52 |

[a] See Table 2. Percentage of agreement between susceptibility profile and conventional procedures was 97.3%.
[b] For abbreviation, see Table 3.

TABLE 5

| Group affiliation by susceptibility profile and conventional procedures - 14 variables[a] | | | | | | | | | |
|---|---|---|---|---|---|---|---|---|---|
| Group affiliation by conventional procedures | Group affiliation by susceptibility profile | | | | | | | | |
| | CITROB[b] | ENTEROB | ECOLI | HEREL | KLEB | PROTMIR | PROTOTH | PSEUDO | SERRAT |
| CITROB | 42 | 4 | 2 | 0 | 1 | 0 | 1 | 0 | 0 |
| ENTEROB | 2 | 44 | 2 | 0 | 0 | 0 | 0 | 0 | 0 |
| ECOLI | 1 | 1 | 72 | 0 | 0 | 0 | 0 | 0 | 0 |
| HEREL | 0 | 0 | 0 | 35 | 0 | 0 | 0 | 0 | 0 |
| KLEB | 0 | 1 | 1 | 0 | 57 | 0 | 0 | 0 | 0 |
| PROTMIR | 0 | 0 | 0 | 0 | 0 | 51 | 0 | 0 | 0 |
| PROTOTH | 0 | 0 | 0 | 0 | 0 | 1 | 48 | 0 | 0 |
| PSEUDO | 0 | 0 | 0 | 0 | 1 | 0 | 0 | 61 | 0 |
| SERRAT | 0 | 1 | 0 | 0 | 0 | 0 | 1 | 0 | 50 |

[a] Variables included ampicillin, bacitracin, carbenicillin 50 and 120, cephalothin, colistin 2 and 13, erythromycin 15, kanamycin 5, methenamine mandelate, neomycin 5, nitrofurantoin, novobiocin 30, and tetracycline 0.5. Percentage of agreement with conventional procedures was 95.6%.
[b] For abbreviations, see Table 3.

SUMMARY

This study was undertaken to determine the feasibility of using susceptibility profiles for the identification of bacteria. Within the scope of the study, this objective was successfully accomplished; the feasibility of this method was proved. To prevent dilution of effort in a large number of non-antibiotic chemical compounds are being examined for their ability to differentiate bacterial groups by differential inhibition of growth. One of the criteria for selection is that the compound not be commonly used in the clinical setting to minimize the possibility of acquired resistance. If bacteria do not normally encounter an agent in their environment, acquired resistance should not become a problem. We have also more than doubled the number of bacterial groups being studied, both by additional genera and increased speciation.

In summary, this study has shown that identification of bacteria using their relative susceptibility to various antimicrobial agents is a practicable approach.

The photometer 10 has been designed to facilitate computer interfacing. Available as either a factory or field installed option is a computer interface kit that enables the instrument to be connected to a computer system. The computer system contains the bacteria-identifying data bank and other useful data and performs the identification by the aforementioned statistical analyses of the input data measured by the photometer.

We claim:

1. A method of identifying a strain of microorganism in a liquid sample comprising the steps of dividing the sample into at least 18 sub-samples, inoculating each of the sub-samples with a growth-inhibiting agent whose reaction with the sub-samples has characteristics capable of identifying the strain of microorganism in said sample, the identity and/or quantity of the growth-inhibiting agent inoculated into each of said sub-samples being different, incubating the sub-samples to develop potentially significant differences in the growth of microorganism in each of them, reading a measure of the growth of the microorganism in each sub-sample, and comparing the growth readings with a bank of microorganism-identifying data relative to said growth-inhibiting agents by quadratic discriminant function analysis, whereby the strain of microorganism in the sample is identified, said growth-inhibiting agents being selected from the group consisting of acriflavine, 9-amino-acridine, auramine O, brilliant green, cetrimide, cobalt chloride, cupric chloride, cycloserine, 3,5-dibromosalicylic acid, dodecylamine hydrochloride, 5-fluorouracil, floxuridine, malachite green, methylene blue, omadine disulfide, sodium omadine, sodium azide, thallous acetate, 2',3',4'-trihydroxyacetophenone, bacitracin, carbenicillin, cephalothin, colistin, kanamycin, methenamine mandelate, nalidixic acid, nitrofurantoin, novobiocin, polymyxin B and tetracycline.

2. A method of claim 1, wherein said growth readings are obtained photometrically.

3. A method of claim 1 or 2, wherein one additional sub-sample is maintained free of a growth-inhibiting agent, said additional sub-sample being used as a control sub-sample.

4. A method of claim 3, wherein the concentrations of growth-inhibiting agents in the inoculated sub-samples are approximately as follows: acriflavine (5 or 20 mcg./ml), 9-aminoacridine (6.7 mcg./ml.), auramine O (107 mcg./ml.), brilliant green (1,2 or 3.3 mcg./ml.), cetrimide (80 mcg./ml.), cobalt chloride (250 mcg./ml.), cupric chloride (250 mcg./ml.), cycloserine (80 or 160 mcg./ml.), 3,5-dibromosalicylic acid (500 mcg./ml.), dodecylamine hydrochloride (12.5 or 50 mcg./ml.), 5-fluorouracil (5.3 mcg./ml.), floxuridine (6 or 24 mcg./ml.), malachite green (2 mcg./ml.), methylene blue (170 mcg./ml.), omadine disulfide (3.7 mcg./ml.), sodium omadine (5 mcg./ml.), sodium azide (50 mcg./ml.), thallous acetate (100 mcg./ml.), 2',3',4'-trihydroxy-acetophenone (250 mcg./ml.), bacitracin (12 units/ml.), carbenicillin (33 mcg./ml.), cephalothin (10 mcg./ml.), colistin (8.7 mcg./ml.), kanamycin (3.3 mcg./ml.), methenamine mandelate (667 mcg./ml.), nalidixic acid (4 mcg./ml.), nitrofurantoin (10 mcg./ml.), novobiocin (20 mcg./ml.), polymyxin B (33 mcg./ml.), tetracycline (0.33 mcg./ml.).

* * * * *